US00PP17832P2

(12) United States Plant Patent
Zaiger et al.

(10) Patent No.: US PP17,832 P2
(45) Date of Patent: Jun. 26, 2007

(54) INTERSPECIFIC TREE NAMED 'AMIGO II'

(50) Latin Name: ***Prunus* sp.**
Varietal Denomination: Amigo II

(76) Inventors: Gary Neil Zaiger, 1907 Elm Ave., Modesto, CA (US) 95358; Leith Marie Gardner, 1207 Grimes Ave., Modesto, CA (US) 95358; Grant Gene Zaiger, 4005 California Ave., Modesto, CA (US) 95358

( * ) Notice: Subject to any disclaimer, the term of this patent is extended or adjusted under 35 U.S.C. 154(b) by 0 days.

(21) Appl. No.: 11/337,951

(22) Filed: Jan. 24, 2006

(51) Int. Cl.
*A01H 5/00* (2006.01)

(52) U.S. Cl. ..... Plt./180
(58) Field of Classification Search ..... Plt./180, Plt./184
See application file for complete search history.

*Primary Examiner*—Kent Bell
*Assistant Examiner*—June Hwu

(57) ABSTRACT

A new and distinct variety of interspecific tree. The following features of the tree and its fruit are characterized with the tree budded on 'Nemaguard' Rootstock (non-patented), grown on Handford sandy loam soil with Storie Index rating 95, in USDA Hardiness Zone 9, near Modesto, Calif., with standard commercial fruit growing practices, such as pruning, thinning, spraying, irrigation and fertilization. Its novelty consist of the following combination of desirable features:

1. Regular and heavy production of medium size fruit.
2. Fruit with an attractive red skin color.
3. The tree with a vigorous, upright growth habit.
4. Fruit with very good flavor and eating quality.
5. Fruit with a good balance between acid and sugar with an average Brix of 17.6°.
6. Fruit with good shipping and storage trials.

1 Drawing Sheet

Botanical classification: *Prunus* sp. 'Amigo II'.

BACKGROUND OF THE VARIETY

FIELD OF THE INVENTION

In the field of plant genetics, we conduct an extensive and continuing plant-breeding program including the organization and asexual reproduction of orchard trees, and of which plums, peaches, nectarines, apricots, cherries and interspecifics are exemplary. It was against this background of our activities that the present variety of interspecific tree was originated and asexually reproduced by us in our experimental orchard located near Modesto, Stanislaus County, Calif.

PRIOR VARIETIES

The existing variety of interspecific tree, which is known to us, and mentioned herein, 'Flavor Grenade' Interspecific (U.S. Plant Pat. No. 12,097).

ORIGIN OF THE VARIETY

The new and distinct variety of interspecific tree, was originated by us from crosses of the following species, *Prunus salicina*×(*Prunus salicina*×*Prunus armeniaca*) in our experimental orchard located near Modesto, Calif. as a seedling from open pollinated seed of 'Flavor Grenade' Interspecific (U.S. Plant Pat. No. 12,097), the pollen parent is unknown. A large number of these open pollinated seedlings growing on their own root system were planted and under close and careful observation the present seedling exhibited desirable fruit and tree characteristics and was selected in 2000 for asexual propagation and commercialization.

ASEXUAL REPRODUCTION OF THE VARIETY

Asexual reproduction of the new and distinct variety of interspecific tree was by budding to 'Nemaguard' Rootstock (non-patented), as performed by us in our experimental orchard located near Modesto, Calif., and shows that reproductions run true to the original tree and all characteristics of the tree and its fruit are established and transmitted through succeeding asexual propagations.

SUMMARY OF THE NEW VARIETY

The present new variety of interspecific tree [(Plum×(Plumcot))×(Plumcot)]×[(Plum×(Plumcot))]×[unknown pollen] is of large size, vigorous, upright growth and a productive and regular bearer of medium size, yellow flesh fruit with very good flavor and eating quality. The fruit is further characterized by having firm flesh, a good balance between acid and sugar, a average Brix of 17.6° and having good storage and shipping quality. In comparison to its maternal parent 'Flavor Grenade' Interspecific (U.S. Plant Pat. No. 12,097), the fruit of the new variety has a darker, more uniform and attractive red skin color and is approximately 23 days earlier in maturity.

In comparison to the Interspecific 'Dapple Fire' (U.S. Plant Pat. No. 12,409), which is similar in size and shape, the fruit of the new variety has yellow flesh compared to red flesh and is approximately 10 days later in maturity.

PHOTOGRAPH OF THE VARIETY

The accompanying color photographic illustration shows typical specimens of the foliage and fruit of the present new interspecific variety. The illustration shows the upper and lower surface of the leaves, an exterior and sectional view of a fruit divided in its suture plane to show flesh color, pit cavity and the stone remaining in place. The photographic illustration was taken shortly after being picked (shipping ripe) and the colors are as nearly true as is reasonably possible in a color representation of this type.

DESCRIPTION OF THE VARIETY

The following is a detailed botanical description of the new variety of interspecific tree, 5 years of age, its flowers, foliage and fruit, as based on observations of 5 year old specimens grown near Modesto, Calif., with color in accordance with Munsell Book of Color.

Tree:

*Size.*—Large, pruned to 3 to 3.5 meters in height for economical harvesting of fruit. Average spread 3 meters, varies with different cultural practices.

*Vigor.*—Vigorous, growth of 1.5 to 2 meters, the first growing season, varies with type and fertility of soil and climatic conditions.

*Branching habit.*—Upright, crotch angle approximately 30°, increases with heavy crop load.

*Productivity.*—Productive, thinning and spacing of fruit necessary for desired market size fruit.

*Bearer.*—Regular, adequate fruit set 3 consecutive years. No alternate bearing observed.

*Fertility.*—Self sterile, pollinator required.

*Density.*—Medium dense, usually pruned to vase shape to increase sunlight to center of tree to enhance fruit color and health of fruit spurs.

*Hardiness.*—Hardy in all stone fruit growing areas of California. Tree grown in USDA Hardiness Zone 9. Winter chilling requirement approximately 750 hours at or below 45° F.

Trunk:

*Size.*—Medium to large. Average circumference 44.5 cm at 22.8 cm above ground on a 5 year old tree.

*Texture.*—Medium shaggy, increases with age of tree.

*Color.*—Varies from 10YR 6/2 to 10YR 5/2.

Branches:

*Size.*—Medium. Average circumference 14.6 cm at 1.2 meters above ground. Crotch angle approximately 30°, increases with heavy fruit production.

*Surface texture.*—New growth, relatively smooth. Mature growth moderately rough, increasing with age.

*Lenticels.*—Size — small to medium. Average number 44 in a 25.8 sq cm section. Average length 2.5 mm. Average width 1.0 mm. Color varies from 7.5YR 6/10 to 7.5YR 6/12.

*Color.*—New growth varies from 2.5GY 5/6 to 2.5GY 4/6. Mature growth varies from 7.5YR 6/2 to 7.5YR 3/2, varies with age of growth.

Leaves:

*Size.*—Medium to large. Average length 90.0 mm. Average width 41.6 mm.

*Form.*—Oblanceolate.

*Apex.*—Acuminate.

*Base.*—Cuneate.

*Margin.*—Serrulate.

*Thickness.*—Medium.

*Surface texture.*—Upper surface relatively smooth, slight indentations over midrib and leaf veins, glabrous. Lower surface relatively smooth, except for small ridges created by midrib and pinnate venation, glabrous.

*Petiole.*—Size — medium length and width. Average length 15.3 mm. Average width 1.8 mm. Longitudinally grooved. Surface — glabrous. Color — lower surface 2.5GY 5/8. Upper surface 2.5GY 6/10.

*Glands.*—Type — globose. Size — small. Average length 1.0 mm. Average diameter 0.6 mm. Average number 3, varies from 1 to 4. Located on lower portion of leaf blade and upper portion of petiole. Color — varies from 5GY 5/6 to 5GY 5/8.

*Color.*—Upper surface varies from 5GY 3/2 to 7.6GY 3/2. Lower surface varies from 5GY 3/2 to 5GY 4/4. Midrib color varies from 2.5GY 6/4 to 5GY 6/4.

Flower buds:

*Size.*—Small to medium. Average length 10.8 mm. Average diameter 5.1 mm.

*Hardiness.*—Hardy in all stone fruit growing areas of California.

*Form.*—Conical, becoming elongated just before opening.

*Pedicel.*—Size — medium. Average length 9.8 mm. Average width 0.6 mm. Color varies from 2.5GY 6/10 to 5GY 6/6.

*Color.*—N 9.5/ (white).

*Number of buds per spur.*—Average number 5, varies from 2 to 9.

Flowers:

*Size.*—Medium. Average height 10.2 mm. Average diameter 18.4 mm.

*Petals.*—Number 5, alternately arranged to sepals. Size — medium. Average length 10.9 mm. Average width 8.8 mm. Form — obovate. Margin — sinuate. Both upper and lower surfaces glabrous. Color — N 9.5/ (white).

*Sepals.*—Number 5, alternately arranged to petals. Shape — triangular, apex rounded. Size — small. Average length 2.7 mm. Average width 2.6 mm. Both upper and lower surfaces glabrous. Color — upper surface varies from 5GY 6/8 to 5GY 5/10. Lower surface varies from 2.5GY 5/8 to 5GY 6/8.

*Stamens.*—Average number per flower 30. Average filament length 9.2 mm. Filament color N 9.5/ (white). Anther color varies from 10YR 7/10 to 2.5Y 8/10.

*Pollen.*—Present, abundant. Self sterile, pollinator required. Color varies from 2.5Y 7/10 to 5Y 7/10.

*Pistil.*—Normally one. Surface — glabrous. Average length 9.2 mm. Position of stigma average 1.6 mm below anthers. Color varies from 10Y 8/8 to 2.5GY 8/8.

*Fragrance.*—Wanting.

*Blooming period.*—Date of First Bloom Feb. 26, 2004. Date of Petal Fall Mar. 9, 2004, varies slightly with climatic conditions.

*Color.*—N 9.5/ (white).

*Number flowers per flower bud.*—Average 2, varies from 1 to 4.

*Pedicel.*—Size — medium. Average length 10.9 mm. Average width 0.6 mm. Color varies from 2.5GY 6/8 to 2.5GY 6/10.

Fruit:

*Maturity when described.*—Firm ripe.

*Date of first picking.*—Jul. 12, 2004.

*Date of last picking.*—Jul. 17, 2004, varies slightly with climatic conditions.

*Size.*—Medium. Average diameter axially 63.5 mm. Average transversely in suture plane 56.5 mm. Average weight 136.3 grams, varies slightly with fertility of the soil, amount of thinning and climatic conditions.

*Form.*—Slightly elongated.

*Suture.*—Nearly smooth, extends from base to apex.

*Ventral surface.*—Very slightly lipped.

*Apex.*—Nearly rounded, some fruit have slight tip.

*Base.*—Varies from flat to slightly rounded.

*Cavity.*—Rounded to slightly elongated in suture plane. Average depth 7.2 mm. Average diameter 9.6 mm.

Stem:

*Size.*—Large. Average length 15.0 mm. Average diameter 2.4 mm.

*Color.*—Varies from 2.5GY 7/6 to 2.5GY 6/8.

Flesh:

*Ripens.*—Evenly.

*Texture.*—Firm, meaty.

*Fibers.*—Few, small, tender.

*Firmness.*—Firm, nearly as firm as 'Flavor Grenade' Interspecific (U.S. Plant Pat. No. 12,097).

*Aroma.*—Slight.

*Amydgalin.*—Undetected.

*Eating quality.*—Very good.

*Flavor.*—Very good, good balance between acid and sugar.

*Juice.*—Moderate, enhances flavor.

*Brix.*—Average 17.6°, varies slightly with amount of fruit per tree and climatic conditions.

*Color.*—Varies from 2.5Y 8.5/6 to 2.5Y 7.8. Pit cavity 10YR 7/8 to 2.5Y 6/6.

Skin:

*Thickness.*—Medium.

*Surface.*—Smooth.

*Bloom.*—Moderate amount, complete coverage.

*Tendency to crack.*—None.

*Color.*—Ground color varies from 5Y 7/6 to 7.5Y 8/8. Overspread with 5R 3/6 to 7.5R 2/6. Very small, randomly spaced areas of ground color exposed to skin surface giving a speckled pattern to the skin.

*Tenacity.*—Tenacious to flesh.

*Astringency.*—None.

Stone:

*Type.*—Clingstone.

*Size.*—Medium. Average length 26.6 mm. Average width 20.5 mm. Average thickness 10.9 mm.

*Form.*—Obovoid.

*Base.*—Usually flat, varies from flat to rounded.

*Apex.*—Slightly pointed. Average 0.7 mm.

*Surface.*—Very lightly pitted throughout, one long, shallow groove on each side of suture running from base to apex.

*Sides.*—Unequal, one side extending further outward from suture plane.

*Ridges.*—One small, narrow ridge on each side of suture, extending from base to apex.

*Tendency to split.*—None.

*Color.*—Varies from 5YR 4/8 to 7.5YR 4/8 when dry.

Kernal:

*Form.*—Ovate.

*Viability.*—Viable, embryo developed.

*Size.*—Medium. Average length 11.4 mm. Average width 9.4 mm. Average depth 6.1 mm.

*Skin.*—Color varies from 7.5YR 5/6 to 10YR 5/8 when dry.

Use: Dessert. Market — local and long distance.

Keeping quality: Good, held firm 14 days in cold storage at 38° to 42° F. without internal breakdown of flesh or appreciable loss of flavor.

Shipping quality: Good, showed minimal skin scarring or flesh bruising during picking or packing trials.

Plant/fruit disease resistance/susceptibility: No specific testing for relative plant/fruit disease resistance/susceptibility has been designed. Under close observation during planting, growing, and harvesting of fruit, under normal cultural and growing conditions near Modesto, Calif., no particular plant/fruit disease resistance or susceptibility has been observed. Any variety or selection observed during indexing of plant characteristics with abnormal fungus, bacterial, virus or insect susceptibility is destroyed and eliminated from our breeding program.

The present new variety of interspecific tree, its flowers, foliage and fruit herein described may vary in slight detail due to climate, soil conditions and cultural practices under which the variety may be grown. The present description is that of the variety grown under the ecological conditions prevailing near Modesto, Calif.

It is claimed:

1. A new and distinct variety of interspecific tree, substantially as illustrated and described, characterized by its large size, vigorous, upright growth and being a productive and regular bearer of medium size, attractive red skin fruit with very good flavor and eating quality; in comparison to its interspecific maternal parent 'Flavor Grenade' (U.S. Plant Pat. No. 12,097), the fruit of the new variety has a darker, more uniform and attractive red skin color and is approximately 23 days earlier in maturity.

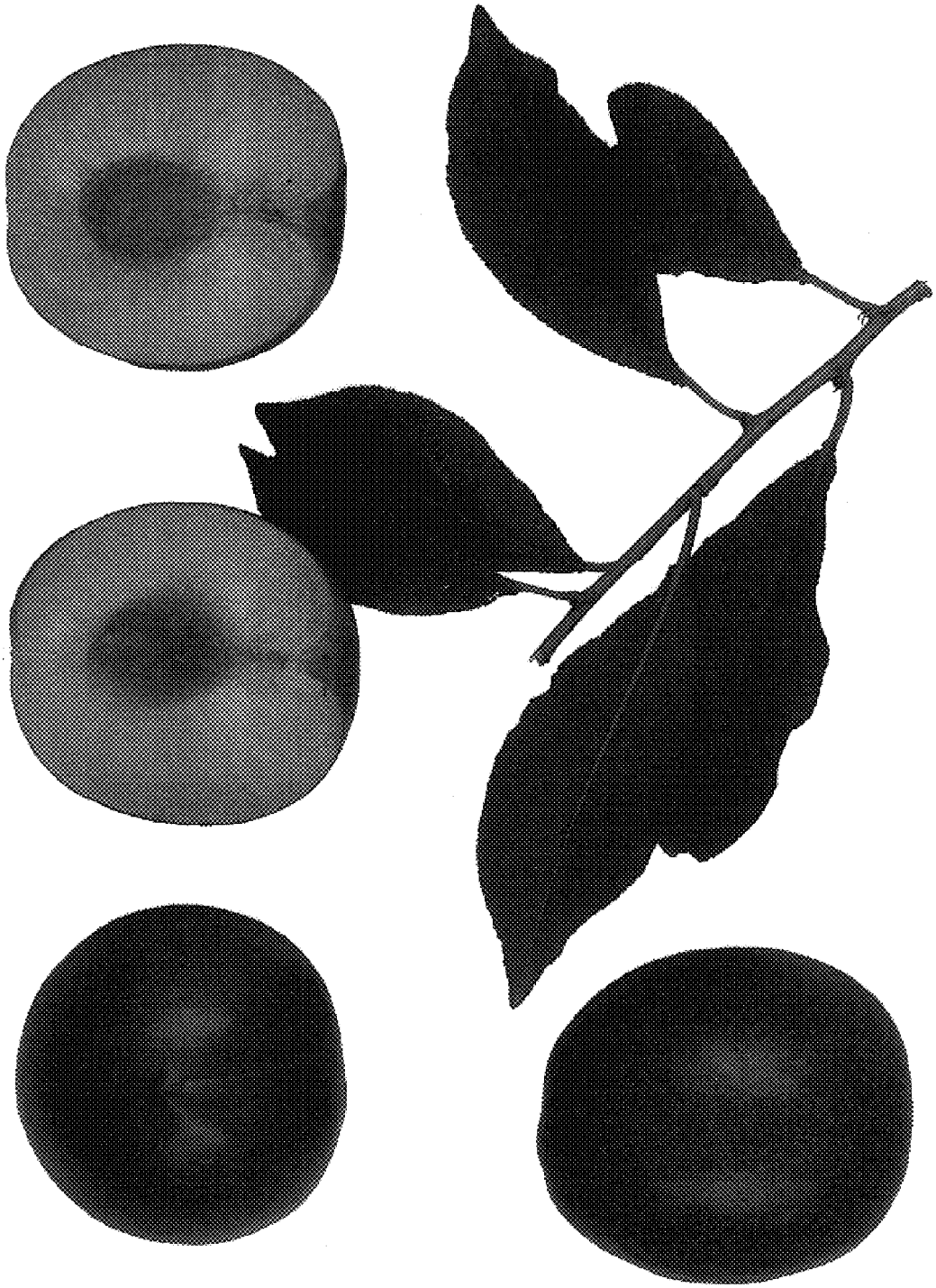

* * * * *